(12) United States Patent
Shaw et al.

(10) Patent No.: US 10,568,554 B2
(45) Date of Patent: Feb. 25, 2020

(54) BLOOD COLLECTION TUBE HOLDER WITH SLIDE-ACTIVATED NEEDLE RETRACTION

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US); Ni Zhu, Plano, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 15/202,179

(22) Filed: Jul. 5, 2016

(65) Prior Publication Data

US 2016/0310057 A1   Oct. 27, 2016

Related U.S. Application Data

(63) Continuation-in-part of application No. 14/020,465, filed on Sep. 6, 2013, now Pat. No. 9,956,352, which
(Continued)

(51) Int. Cl.
*A61B 5/15*   (2006.01)
*A61M 5/32*   (2006.01)
(Continued)

(52) U.S. Cl.
CPC .... *A61B 5/150656* (2013.01); *A61B 5/15003* (2013.01); *A61B 5/154* (2013.01);
(Continued)

(58) Field of Classification Search
CPC ............ A61M 5/32; A61M 2005/3206; A61M 5/322; A61M 5/3221
See application file for complete search history.

(56) References Cited

U.S. PATENT DOCUMENTS 4,466,446 A   8/1984   Baidwan et al.
4,747,831 A   5/1988   Kulli
(Continued)

FOREIGN PATENT DOCUMENTS

CN   1155846   7/1995
EP   0479303   8/1992
(Continued)

*Primary Examiner* — Daniel L Cerioni
*Assistant Examiner* — Yasmeen S Warsi
(74) *Attorney, Agent, or Firm* — Ross Barnes LLP; Monty L. Ross

(57) ABSTRACT

A blood collection tube holder embodying two coaxially alignable needles, the first needle being a forwardly facing venipuncture needle and the second needle being a rearwardly facing fluid discharge needle. The first and second needles are satisfactorily supported by a frontal attachment and body, respectively, that are disposed in relative sliding engagement along an interface that is transverse to the first and second needle and that extends at least from the second needle to an opening into a needle retraction chamber that projects rearwardly from the body. The subject device is configured to receive and support a conventional blood collection tube of the type used to collect blood samples.

18 Claims, 17 Drawing Sheets

Related U.S. Application Data is a continuation-in-part of application No. 13/714,819, filed on Dec. 14, 2012, now Pat. No. 9,138,545.

(60) Provisional application No. 61/737,263, filed on Dec. 14, 2012, provisional application No. 61/836,723, filed on Jun. 19, 2013.

(51) Int. Cl.
*A61B 5/154* (2006.01)
*A61M 25/06* (2006.01)

(52) U.S. Cl.
CPC .. *A61B 5/150259* (2013.01); *A61B 5/150351* (2013.01); *A61B 5/150389* (2013.01); *A61B 5/150496* (2013.01); *A61B 5/150503* (2013.01); *A61B 5/150572* (2013.01); *A61B 5/150587* (2013.01); *A61B 5/150709* (2013.01); *A61B 5/150717* (2013.01); *A61B 5/150732* (2013.01); *A61B 5/150885* (2013.01); *A61M 5/3232* (2013.01); *A61M 5/3202* (2013.01); *A61M 25/0606* (2013.01); *A61M 25/0631* (2013.01); *A61M 2005/3227* (2013.01)

(56) References Cited

U.S. PATENT DOCUMENTS

| | | |
|---|---|---|
| 4,813,426 A | 3/1989 | Haber et al. |
| 4,813,935 A | 3/1989 | Haber et al. |
| 4,941,883 A | 7/1990 | Venturini |
| 4,973,316 A | 11/1990 | Dysarz |
| 5,052,403 A | 10/1991 | Haber et al. |
| 5,085,640 A | 2/1992 | Gibbs |
| 5,163,916 A | 11/1992 | Sunderland |
| 5,263,942 A | 11/1993 | Smedley et al. |
| 5,298,023 A | 3/1994 | Haber et al. |
| 5,370,628 A | 12/1994 | Allison et al. |
| 5,395,337 A | 3/1995 | Clemens et al. |
| 5,423,758 A | 6/1995 | Shaw |
| 5,445,618 A | 8/1995 | Adobbati |
| 5,498,245 A | 3/1996 | Whisson |
| 5,503,010 A | 4/1996 | Yamanaka |
| 5,573,510 A | 12/1996 | Isaacson |
| 5,685,863 A | 11/1997 | Botich et al. |
| 5,704,920 A | 1/1998 | Gyure |
| 5,728,073 A | 3/1998 | Whisson |
| 5,779,679 A | 7/1998 | Shaw |
| 5,795,339 A | 8/1998 | Erskine |
| 5,810,775 A | 9/1998 | Shaw |
| 5,957,887 A | 9/1999 | Osterlind et al. |
| 5,964,731 A | 10/1999 | Kovelman |
| 6,039,713 A | 3/2000 | Botich et al. |
| 6,063,040 A | 5/2000 | Owen et al. |
| 6,210,371 B1 | 4/2001 | Shaw |
| 6,277,102 B1 | 8/2001 | Carilli |
| 6,468,250 B2 | 10/2002 | Yang |
| 6,794,423 B1 | 9/2004 | Li |
| 6,808,512 B1 | 10/2004 | Lin et al. |
| RE39,107 E | 5/2006 | Shaw |
| 7,351,224 B1 | 4/2008 | Shaw |
| D645,962 S | 9/2011 | Shaw et al. |
| D660,420 S | 5/2012 | Shaw et al. |
| 8,292,852 B2 | 10/2012 | Mulholland |
| 8,343,094 B2 | 1/2013 | Shaw |
| 2001/0021827 A1 | 9/2001 | Ferguson et al. |
| 2002/0068907 A1 | 6/2002 | Dysarz |
| 2002/0082560 A1 | 6/2002 | Yang |
| 2002/0165498 A1 | 11/2002 | Ward, Jr. |
| 2003/0078540 A1 | 4/2003 | Saulenas et al. |
| 2003/0171695 A1 | 9/2003 | Zurcher |
| 2003/0181871 A1 | 9/2003 | Wilkinson et al. |
| 2003/0236504 A1 | 12/2003 | Chen |
| 2004/0015135 A1 | 1/2004 | Wilkinson |
| 2004/0019329 A1 | 1/2004 | Erskine |
| 2004/0133172 A1 | 7/2004 | Wilkinson |
| 2004/0204688 A1 | 10/2004 | Lin et al. |
| 2004/0249309 A1 | 12/2004 | Yang et al. |
| 2005/0004524 A1 | 1/2005 | Newby et al. |
| 2005/0267384 A1 | 12/2005 | Sauer et al. |
| 2005/0288607 A1 | 12/2005 | Konrad |
| 2006/0155244 A1* | 7/2006 | Popov ............... A61M 25/0625 604/162 |
| 2006/0189934 A1 | 8/2006 | Kuracina et al. |
| 2006/0235354 A1 | 10/2006 | Kaal et al. |
| 2007/0260189 A1 | 11/2007 | Shaw et al. |
| 2008/0132851 A1 | 6/2008 | Shaw et al. |
| 2008/0132854 A1 | 6/2008 | Sharp |
| 2008/0287881 A1 | 11/2008 | Kiehne |
| 2008/0319345 A1 | 12/2008 | Swenson |
| 2009/0198196 A1 | 8/2009 | West et al. |
| 2009/0204026 A1 | 8/2009 | Crawford et al. |
| 2009/0306601 A1 | 12/2009 | Shaw et al. |
| 2010/0000040 A1 | 1/2010 | Shaw et al. |
| 2010/0003067 A1 | 1/2010 | Shaw et al. |
| 2010/0241029 A1 | 9/2010 | Mahurkar |
| 2010/0286604 A1 | 11/2010 | Shaw |
| 2010/0317999 A1 | 12/2010 | Shaw et al. |
| 2011/0264037 A1 | 10/2011 | Foshee et al. |
| 2012/0016307 A1 | 1/2012 | Burkholz et al. |
| 2012/0022464 A1 | 1/2012 | Zivkovic et al. |
| 2012/0071790 A1 | 3/2012 | Mahurkar |
| 2012/0071827 A1 | 3/2012 | Zivkovic et al. |
| 2012/0078225 A1 | 3/2012 | Zivkovic et al. |
| 2012/0226232 A1 | 9/2012 | Shaw et al. |
| 2012/0259243 A1 | 10/2012 | Shaw et al. |
| 2012/0316466 A1 | 12/2012 | Crawford et al. |
| 2014/0171878 A1 | 6/2014 | Shaw et al. |
| 2014/0276445 A1 | 9/2014 | Shaw et al. |

FOREIGN PATENT DOCUMENTS

| | | |
|---|---|---|
| EP | 1161962 | 12/2001 |
| WO | WO2005087102 | 9/2005 |

* cited by examiner

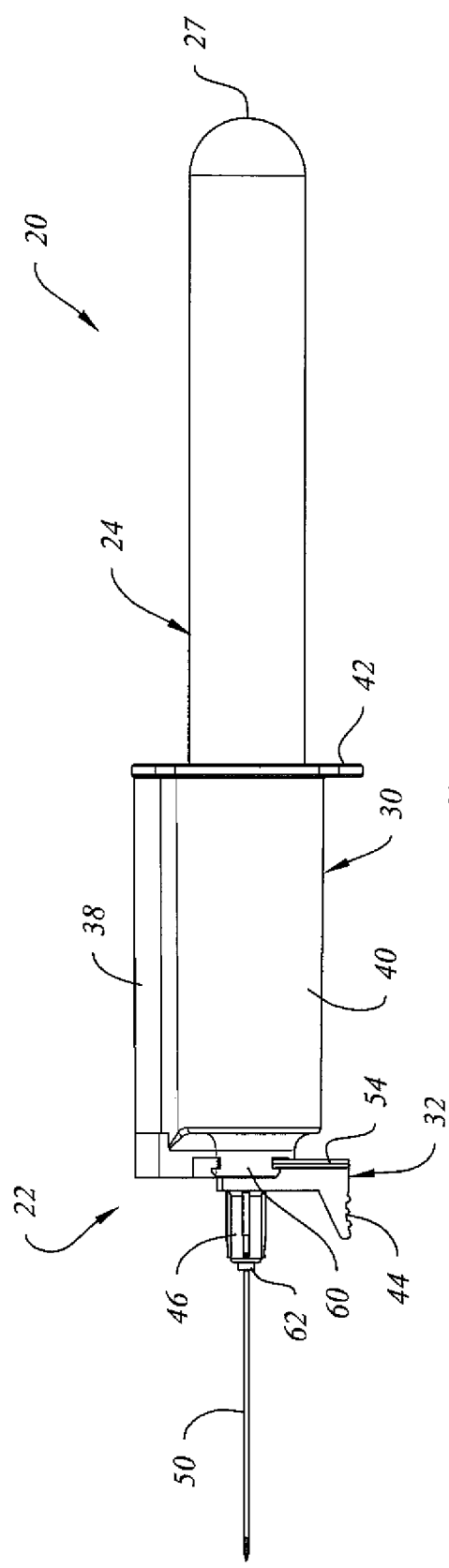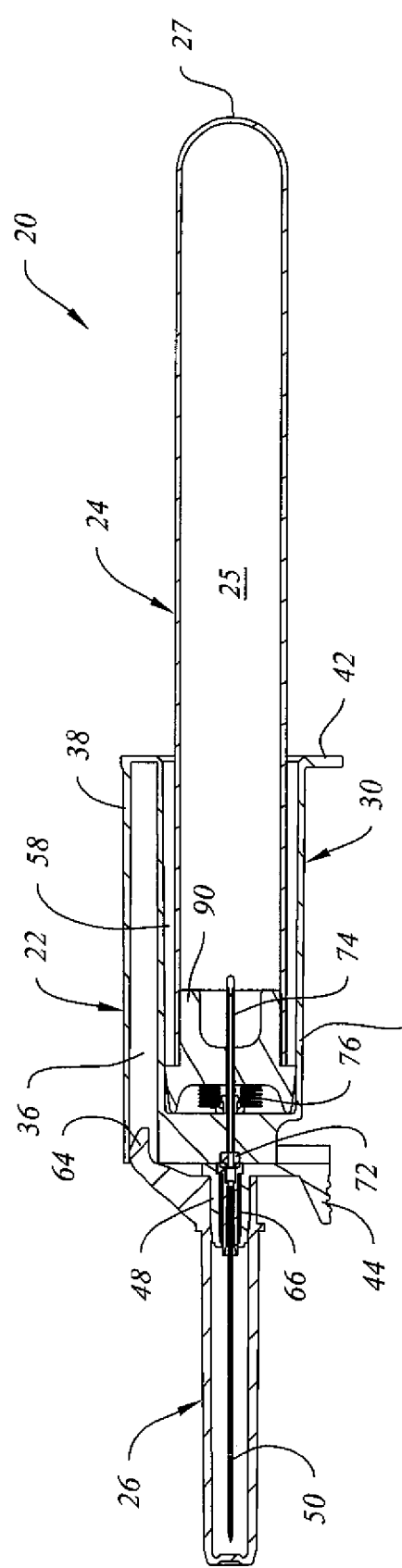

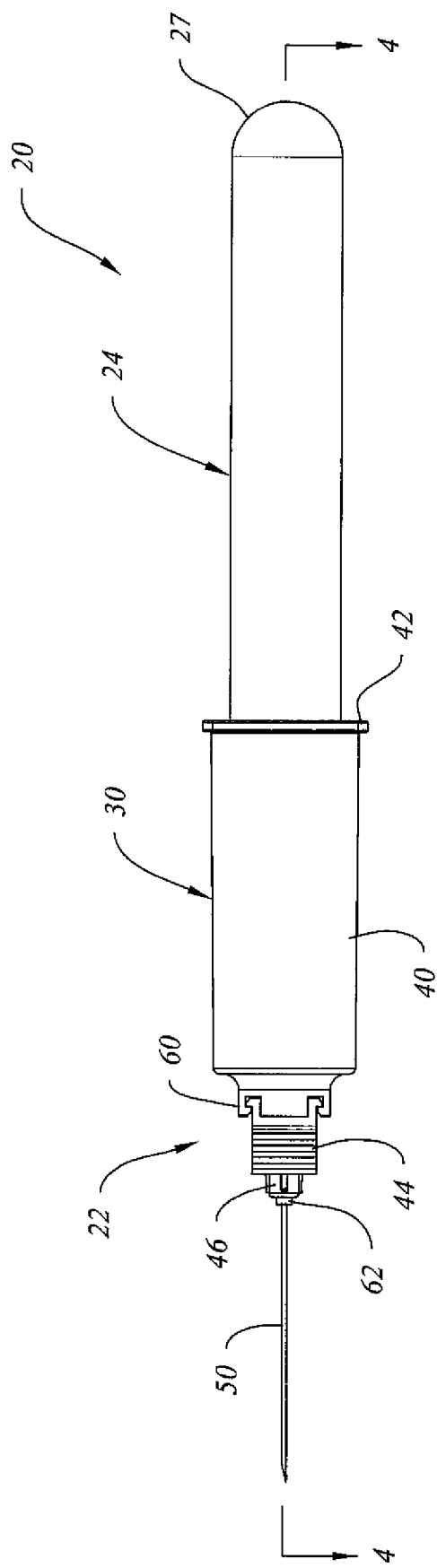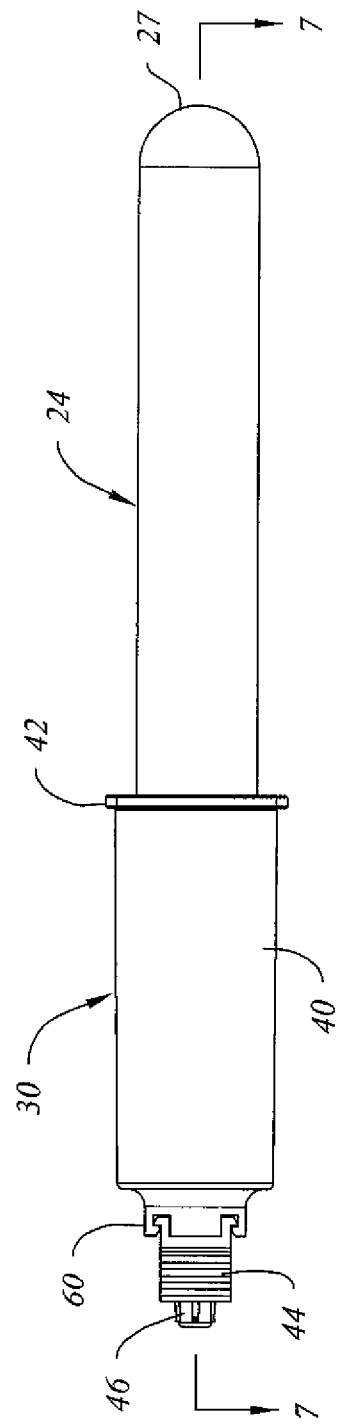

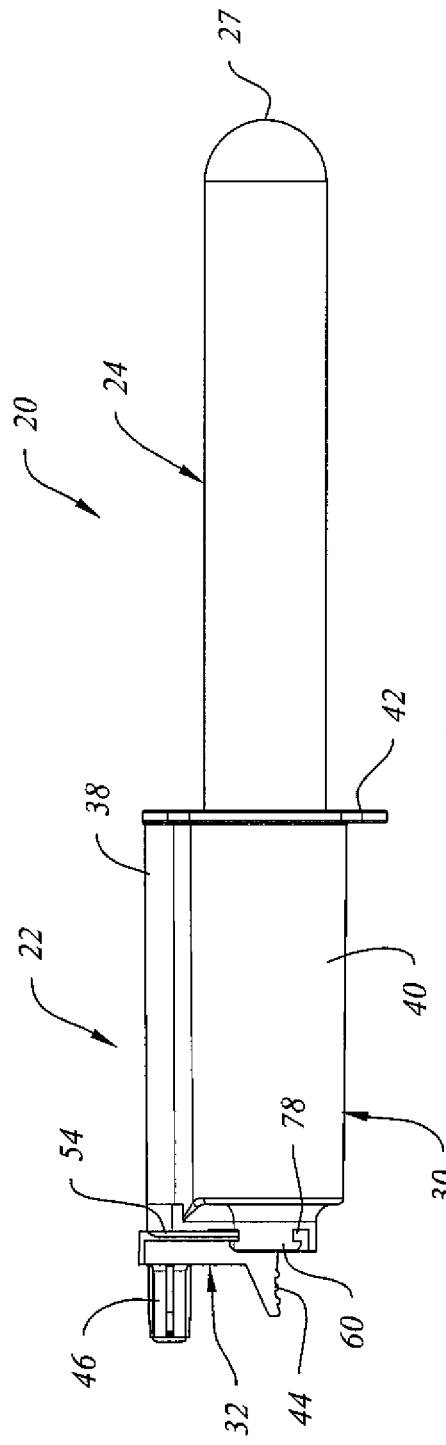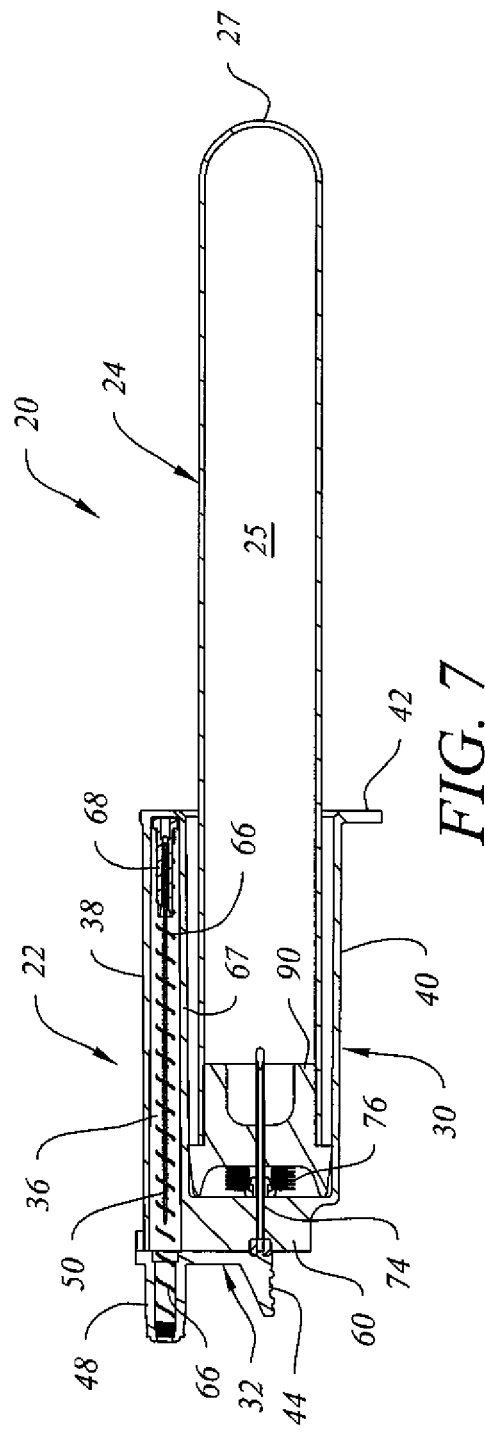

BLOOD COLLECTION TUBE HOLDER WITH SLIDE-ACTIVATED NEEDLE RETRACTION

BACKGROUND OF THE INVENTION

1. Field of the Invention

This invention is a medical device configured for use in drawing and collecting samples of bodily fluids, and especially vascular fluids such as blood. One aspect of the invention relates to a fluid collection tube holder comprising two longitudinally separated, oppositely facing, preferably coaxially alignable, needles. One needle faces forwardly and is suitable for insertion into a patient. The other needle faces rearwardly and is suitable for insertion into a collection tube for bodily fluids that is preferably evacuated. A flash chamber is desirably but not necessarily provided between the two needles to alert the user that the forwardly facing needle tip is positioned so that a bodily fluid is flowing through the needle.

Another aspect of the invention is a blood collection tube holder having slide-activated needle retraction that is selectively initiated by the concurrent application of digital pressure to opposite sides of the device, and wherein the invention comprises a sliding interface disposed between opposed and facing surfaces of a body and a frontal attachment, and transverse to the direction of fluid flow through the device.

Another aspect of the invention is a medical device having a body, a frontal attachment disposed in transverse sliding engagement with the body, two oppositely directed, coaxially aligned needles seated in the body and in the frontal attachment, respectively, and a needle retraction chamber in the body that is offset laterally from a fluid flow path through the body. Following collection of a fluid sample, the user initiates relative sliding movement along an interface between the body and the frontal attachment that is transverse to the original fluid flow path. This movement realigns the forwardly facing needle with the needle retraction chamber so that the forwardly facing needle is retracted into the needle retraction chamber and the associated needle tip is no longer exposed, thereby lessening the likelihood of accidental needle stick injury and the possibility of contamination by fluid-borne pathogens. Needle retraction can optionally be achieved before or after withdrawing the forwardly projecting needle from the patient and before or after withdrawing a fluid collection tube (such as a Vacutainer® blood collection tube often used during venipuncture procedures) from a patient's vein.

According to another aspect of the invention, optional structures useful for avoiding premature lateral repositioning of the body relative to the frontal attachment are also disclosed. Such structures can include, for example and without limitation, a locking cap that engages the body or another rupturable, breakable, frangible, frictionally engageable or otherwise selectively displaceable physical barrier that restricts premature transverse lateral movement of the frontal attachment relative to the body of the device.

2. Description of Related Art

U.S. Pat. No. 5,810,775 and RE39,107 disclose Medical devices such as blood collection tube holders having a single double-ended needle that is retractable into the cylindrical body of the tube holder following use. Needle retraction is initiated by closing a hinged cap upon removal of a fluid collection tube, which causes a coaxially aligned inner sleeve to move forwardly and release a rearwardly biased needle.

U.S. D645,962 and U.S. D660,420 disclose a housing for a collection device for bodily fluids that comprises a substantially cylindrical section having a forwardly extending cylindrical nose, an open rear end, a plurality of longitudinally extending ribs disposed on each side of the cylindrical section, and an elongate arm pivotably mounted near the rear of the housing over an upwardly facing slot in the tube holder.

U.S. Pat. No. 8,496,600 discloses a non-reusable collection device for bodily fluids such as vascular blood, the device having a housing configured similarly to that of U.S. D645,962, wherein a single, rearwardly biased double-ended needle is constrained prior to needle retraction by a rotatably mounted lug ring. The needle is released during retraction by depressing a pivotably mounted trigger connected to the body of the device to contact and rotate the lug ring, after which the needle holder is driven into a retraction cavity disposed inside the trigger while the trigger is disposed at an angle that intersects the central longitudinal axis through the housing U.S. Pat. No. 9,247,899 discloses a blood draw device with a single, double-ended retractable needle that is similar in form and function to the device of U.S. Pat. No. 8,496,600 except that a retainer clip retains the rearwardly biased double-ended needle until the front portion of an actuator (similar to the trigger of the '600 patent) is pivoted downwardly to cause the retainer clip to release the needle holder, after which a compressed spring expands and drives the needle holder into a retraction cavity inside the actuator that is disposed at an angle that intersects the central longitudinal axis through the housing.

U.S. Pat. No. 8,469,927 discloses an actuator that moves relative to the housing but does not have a rearwardly facing needle and is not disclosed for use with a fluid collection tube insertable into the housing.

SUMMARY OF THE INVENTION

The medical device of the invention satisfactorily comprises a forwardly projecting venipuncture needle, a fluid collection tube holder comprising a second rearwardly facing needle suitable for insertion into a vascular fluid collection tube, a needle retraction mechanism configured to render the forwardly projecting needle tip safe following use, and a needle retraction chamber that is laterally offset from and is transversely moveable into coaxial alignment with the forwardly projecting needle following use to interrupt the fluid flow path between the two needles and initiate retraction of the forwardly facing needle into the needle retraction chamber.

According to an embodiment of the invention, the subject medical device further comprises a body having at least two forwardly facing openings, including one opening to a bore that is coaxially aligned with a rearwardly facing needle seated inside the body and another opening that provides access to the front end of an elongated needle retraction chamber facing rearwardly from the body. In one embodiment, the opening into the needle retraction chamber is also engageable with a rearwardly projecting locking lug of a locking needle cap disposed over the forwardly projecting needle prior to use of the device. Optionally, in another embodiment, the body can have a third forwardly facing opening situated between the two forwardly facing openings mentioned above that is configured to receive a rearwardly projecting locking lug of a locking needle cap disposed over the forwardly projecting venipuncture needle prior to use of the device.

According to an embodiment of the invention, the subject medical device comprises a frontal attachment having a rearwardly biased, forwardly projecting needle that is supported by a needle retraction mechanism disposed inside a stepped bore in the frontal attachment that is coaxially alignable with a rearwardly facing needle seated in the body during assembly of the device. The frontal attachment is desirably slidably engageable with the body to form a sliding interface formed between a forwardly facing surface of the body and a rearwardly facing surface of the frontal attachment, with the sliding interface being along a plane that is generally transverse to a fluid flow path through the forwardly projecting and rearwardly facing needles when they are coaxially aligned. When configured in this manner, relative sliding movement between the body and the frontal attachment in the transverse plane can be selectively initiated by a user to reposition the needle retraction chamber relative to the frontal attachment and the forwardly projecting needle.

Needle retraction is desirably achieved by applying oppositely directed pressure to generally opposed touch surfaces of the body and frontal attachment, respectively, to reposition the opening into the needle retraction cavity into substantial coaxial alignment with the rear of the forwardly facing needle. Although either or both of the body and frontal attachment can slide relative to the other by applying digital pressure to the touch surfaces of each whenever the forwardly projecting needle is not inserted into a patient, lateral sliding movement of the body relative to the frontal attachment is desirable whenever the forwardly projecting needle remains inserted in a patient during retraction. This is accomplished by applying only a resistive force to the touch pad of the frontal attachment while also applying an oppositely directed force to the touch pad of the body that is sufficient to slide the forwardly facing opening of the needle retraction chamber toward and into coaxial alignment with the rear end of the forwardly facing needle. By retracting the forwardly projecting needle directly from a patient, a user can reduce the likelihood of dripping or splattering blood from the needle or an accidental needle stick and the associated risk of spreading blood-borne pathogens as compared to first withdrawing the forwardly facing needle from the patient and then initiating retraction.

According to an embodiment of the invention, the body of the subject medical device can include a substantially cylindrical fluid collection tube holder that is coaxially aligned with the rearwardly facing needle and an integrally molded needle retraction chamber that is offset laterally from the fluid collection tube holder but has a longitudinal axis that is substantially parallel to the fluid flow path through the rearwardly facing needle. According to another embodiment of the invention, the body of the subject medical device includes a needle retraction cavity that is unitarily molded and shares a common wall with a substantially cylindrical fluid collection tube holder.

According to an embodiment of the invention, the body of the subject medical device can comprise a rearwardly facing needle retraction chamber and a laterally spaced-apart attachment structure such as a threaded connector that is cooperatively engageable with a similarly but oppositely configured threaded connector of a generally cylindrical fluid collection tube holder having a rearwardly facing opening cooperatively sized and configured to receive and support a conventional fluid collection tube. It will also be apparent to those of skill in the art reading this disclosure that other similarly effective means for receiving and supporting a fluid collection tube holder in fluid communication with a fluid flow path through the forwardly projecting and rearwardly facing needles of the subject device can also be used within the scope of the invention disclosed here.

According to another embodiment of the invention, the body of the subject medical device can comprise an interference element that provides resistance to relative sliding movement between the body and the frontal attachment that is sufficient to prevent the body or frontal attachment from being accidentally or inadvertently shifted laterally to a position that will allow the forwardly facing needle to retract prematurely once the locking needle cap has been removed. The interference element can, for example, be a small protrusion or projection extending outwardly from the forwardly facing surface of the body in a position that contacts a portion of the frontal attachment and provides sufficient resistance to relative sliding movement that premature needle retraction is avoided until the pressure applied to the touch pads of the body and frontal attachment is sufficient to overpressure the resistance and permit movement to a point where needle retraction can occur. As another example, the interference element can be a weak connecting structure or a small bridging member that maintains the body and frontal attachment in a relative position where the forwardly projecting needle is coaxially aligned with the rearwardly facing needle until the bridging member is dislodged, repositioned, cut, severed, fractured, ruptured, torn, frictionally disengaged or otherwise rendered ineffective for interfering with relative sliding movement between the body and the frontal attachment sufficiently to permit needle retraction.

According to an embodiment of the invention, when the body is molded from a substantially transparent polymeric material, a flash chamber can optionally be provided between the forwardly projecting needle and the rearwardly facing needle to provide visual confirmation of the presence of fluid between the needles and alert the user that the tip of the forwardly facing needle is properly positioned to receive fluid flow from the patient's body.

According to an embodiment of the invention, the body of the subject medical device is desirably configured to receive and support a blood collection tube and further comprises a rearwardly facing needle and a laterally offset needle retraction cavity. The frontal attachment desirably comprises a forwardly facing needle and a needle retraction mechanism. During use, the forwardly facing needle and the rearwardly facing needle are desirably coaxially aligned and cooperate in forming a fluid flow path from a patient to a blood collection tube. Following use, the body of the device is moved laterally in relation to the frontal attachment to reposition the forwardly facing needle into coaxial alignment with the needle retraction cavity to initiate retraction of the forwardly facing needle into the needle retraction cavity of the body sufficiently to prevent the tip of the forwardly facing needle from projecting forwardly out of the forwardly facing opening in the frontal attachment.

One embodiment of the invention relates to a fluid collection tube holder useful in obtaining samples of bodily fluids, the tube holder desirably comprising a body that is releasably engageable with a fluid collection tube, a frontal attachment disposed in transverse sliding engagement with the body, a first needle facing rearwardly from the body, and a second needle projecting forwardly from the frontal attachment, the first and second needles cooperating with the body and the frontal attachment to establish a fluid flow path from a fluid source to a fluid collection tube operatively engaging the body. Another embodiment of the invention comprises a fluid collection tube holder having a body configured to receive and support a fluid collection tube, the body also having a needle retraction chamber with a forwardly facing opening that is offset laterally from a fluid flow path through the body and into the fluid collection tube, and a common wall disposed between the fluid collection tube holder and the needle retraction chamber.

Another embodiment of the invention relates to a fluid collection tube holder having two coaxially aligned, oppositely directed needles, including one non-retractable needle disposed in the body and one retractable needle disposed in a frontal attachment that is slidably engageable with the body along a sliding interface facilitating translational, lateral sliding movement in a direction that is transverse to a fluid flow direction through the coaxially aligned needles. During use of the subject medical device, the body and frontal attachment are desirably cooperatively alignable to establish a substantially linear fluid flow path through the device. Following use of the device and removal of the fluid collection tube, the entire body of the tube holder can be moved transversely and translationally relative to the frontal attachment to initiate needle retraction into a needle retraction chamber that is offset from but parallel to the non-retracting needle disposed in the body.

Another embodiment of the invention relates to a medical device having two separate needles, including a first needle seated in the body and having a rearwardly facing tip, and a second needle seated in the frontal attachment and having a forwardly facing tip. Another embodiment of the invention relates to a medical device having a forwardly facing needle, a rearwardly facing needle, and a flash chamber disposed between the two needles.

This section of the application also incorporates by reference into this Summary of the Invention the statements previously made in the section of this patent application subtitled "Technical Field." These and other features, objects and advantages of the present invention will become better understood from a consideration of the following detailed description of the preferred embodiments and appended claims in conjunction with the drawings.

BRIEF DESCRIPTION OF THE DRAWINGS

The system and method of the invention are further described and explained in relation to the following drawings wherein:

FIG. 3 is a plan view of the medical device of FIG. 1 into which a fluid collection tube has been inserted for use in obtaining a sample of a vascular fluid;

FIG. 4 is a cross-sectional plan view taken along line 4-4 of FIG. 5;

FIG. 5 is a right side elevation view of the medical device of FIG. 3;

FIG. 6 is a plan view of the medical device of FIG. 3 following transverse repositioning of the body relative to the frontal attachment and retraction of the needle, but prior to withdrawal of the fluid collection tube from the body of the subject medical device;

FIG. 7 is a cross-sectional plan view of the medical device of FIG. 6 but taken along line 7-7 of FIG. 9;

FIG. 9 is a right side elevation view of the medical device as in FIG. 5 following transverse repositioning of the body relative to the frontal attachment and retraction of the needle, but prior to withdrawal of the fluid collection tube from the body of the subject medical device;

DETAILED DESCRIPTION

Figure 1:
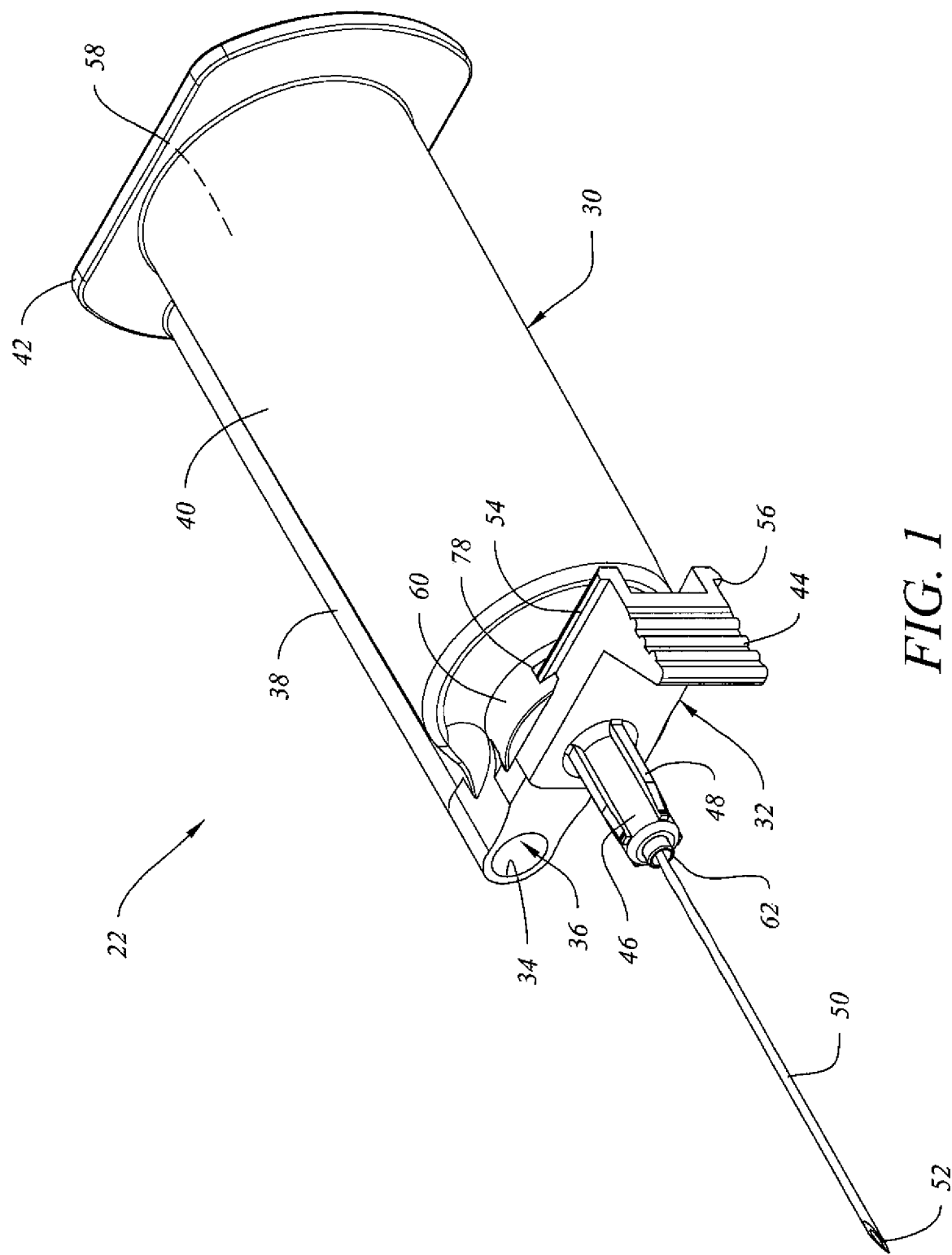
FIG. 1 is a top front perspective view of one embodiment of a medical device of the invention.

Referring to FIGS. 1-9, a bodily fluid sampling device configured as blood collection tube holder 22 desirably comprises body 30 and frontal attachment 32 that are slidably engaged in such manner that body 30 can slide laterally relative to frontal attachment 32. Body 30 further comprises a substantially cylindrical receptacle 40 having an inside bore 58 with a diameter sufficiently large to receive a fluid collection tube (visible in FIGS. 3-7) through a rearwardly facing opening (not visible) surrounded by flange 42. Needle retraction chamber 38 is laterally spaced apart from bore 58 of body 30 and has one open end and one closed end. Needle retraction chamber 38 also comprises an elongate cylindrical bore 36 that is accessed through forwardly facing opening 34. In this embodiment, substantially cylindrical receptacle 40 and needle retraction chamber 38 are unitarily molded of a suitable polymeric material and share a common wall 67 that is best seen in FIG. 7. It should be understood, however, that the longitudinally extending side walls of receptacle 40 and needle retraction chamber 38 can be laterally spaced apart without a common wall. The front portion of body 30 comprises a substantially cylindrical collar 60 comprising upper and lower slots 78 configured to receive and support top and bottom rails 54, 56 respectively, of frontal attachment 32 to facilitate lateral sliding movement of body 30 relative to frontal attachment 32.

Frontal attachment 32 further comprises digital touchpad 44 facing laterally outward on the side opposite needle retraction chamber. Nose 46 projects forwardly from the slidably engaged portion of frontal attachment 32 and is shown with a plurality of circumferentially spaced, longitudinally extending ribs 48 that provide frictional engagement with a removable needle cap 26 that is shown, for example, in FIGS. 2 and 4. As viewed in FIG. 1, venipuncture needle 50 with beveled needle tip 52 projects forwardly from nose 46. Venipuncture needle 50 is desirably supported by needle holder 68, the forwardly extending tip 62 of which is visible in FIG. 1.

Figure 2:
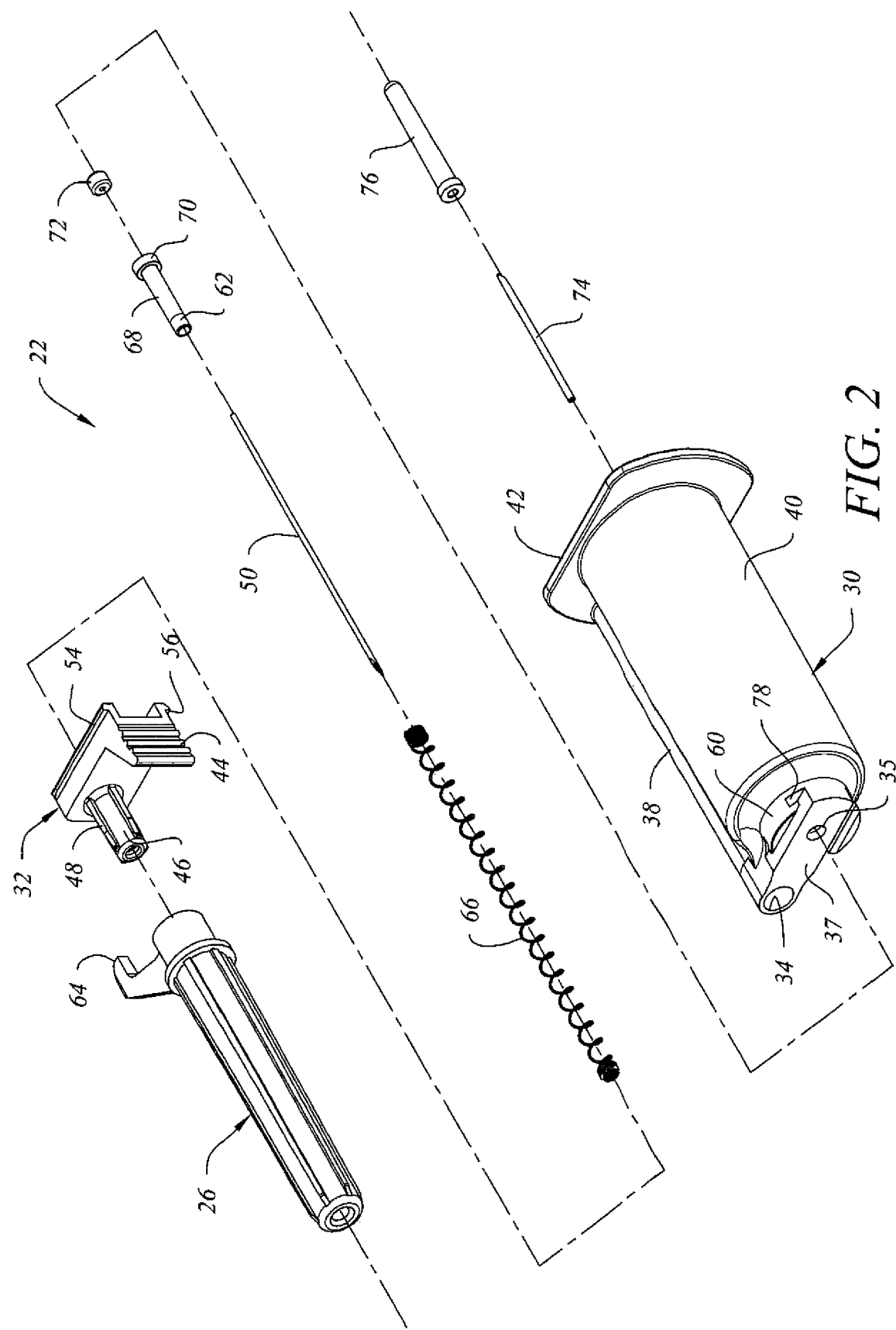
FIG. 2 is an exploded top front perspective view of the medical device of FIG. 1, also showing a locking needle cap that is not depicted in FIG. 1.
Figure 8:
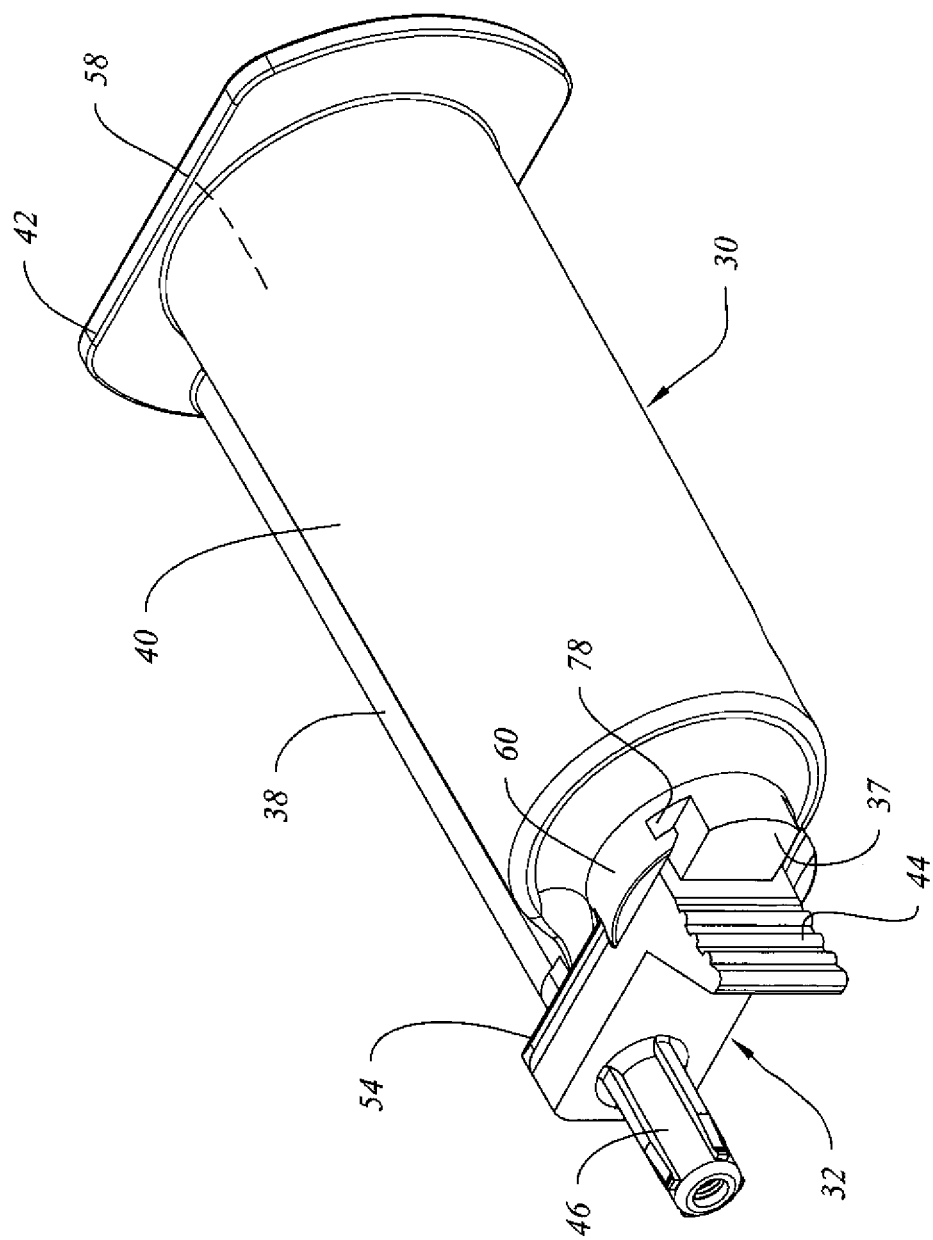
FIG. 8 is a front perspective view of the medical device of FIG. 1 following transverse repositioning of the body relative to the frontal attachment and retraction of the needle, and following withdrawal of the fluid collection tube (shown in FIGS. 3-7 and 9) from the body of the subject medical device.
Figure 10:
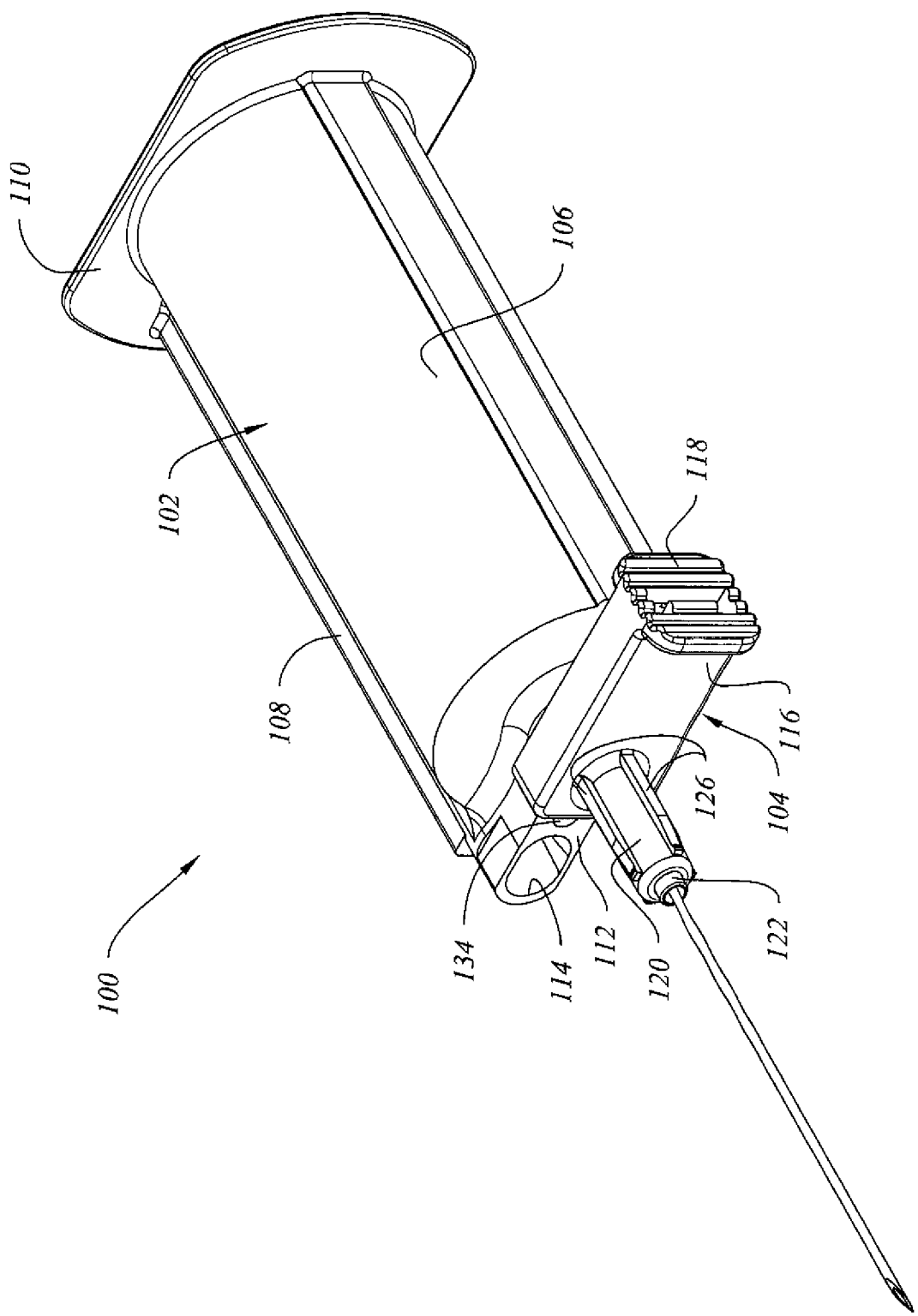
FIG. 10 is a top front perspective view of another embodiment of a medical device of the invention.
Figure 11:
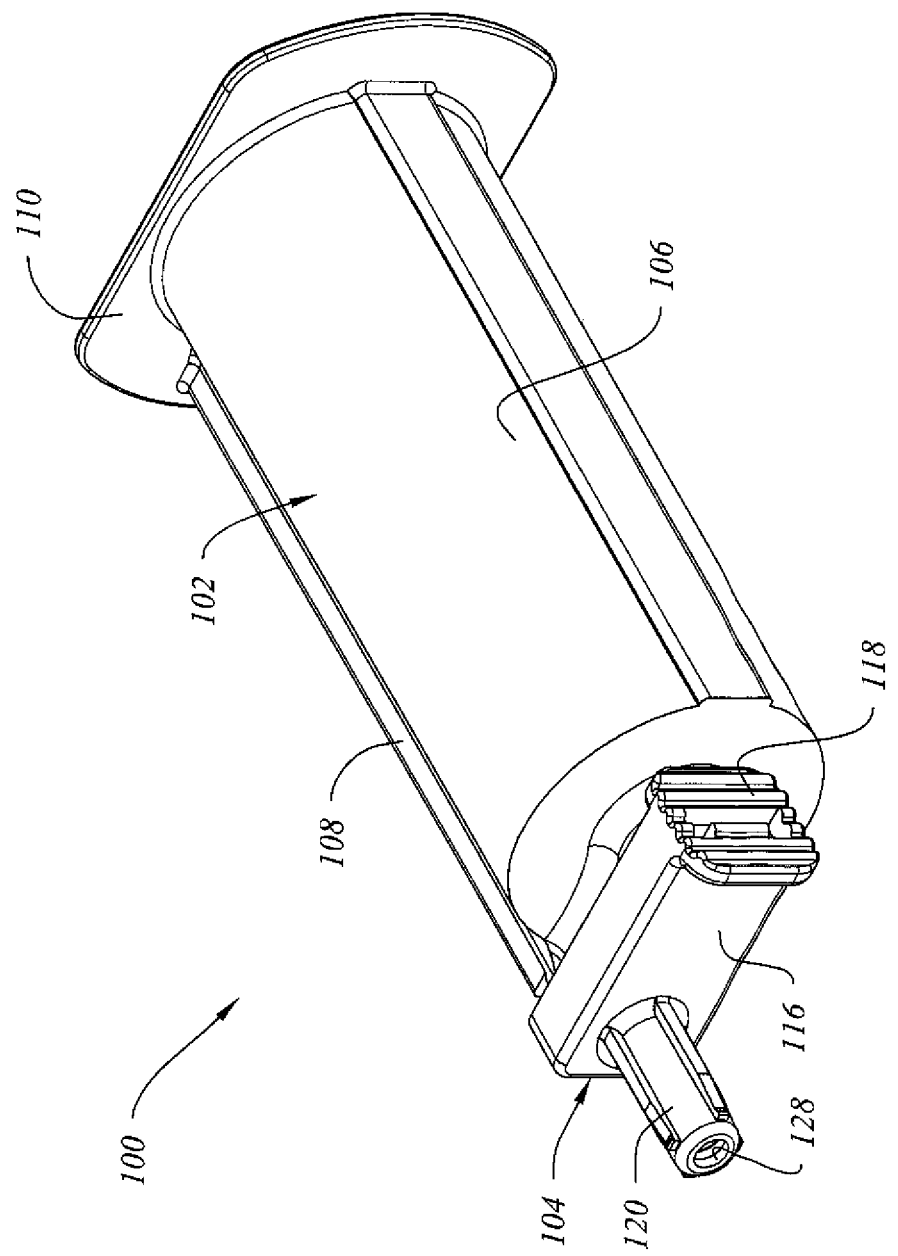
FIG. 11 is a top front perspective view of the medical device of FIG. 10 following transverse repositioning of the body relative to the frontal attachment and retraction of the needle.

Referring to FIG. 2, additional structural elements are visible that are not apparent from FIG. 1. Removable needle cap 26 further comprises locking arm 64 that projects radially outward and has a rearwardly extending tip that is insertable into opening 34 of body 30 when needle cap 26, frontal attachment 32 and body 30 are all assembled as shown in FIG. 4. When in this position, locking arm 64 prevents body 30 and frontal attachment 32 from shifting relative to each other during shipment and storage prior to use. Still referring to FIG. 2, a needle retraction mechanism comprising needle holder 68 and compression spring 66 is desirably seated inside nose 46 of frontal attachment 32 prior to attachment of frontal attachment 32 to body 40. Compression spring 66 has an inside diameter allowing it to slide over needle 50 and onto the elongate shaft portion of needle holder 68. The needle holder also has a larger diameter head 70 that provides a forwardly facing annular surface that abuts against the rearwardly facing end of compression spring 66 to hold the spring in compression when the forwardly facing end of spring 66 is seated inside nose 46.

Fluid seal 72 is desirably seated inside a cylindrical recess 35 that is laterally spaced apart from opening 34 in front surface 37 of body 30. Front surface 37 cooperates with the rearwardly facing surface (not visible in FIG. 2) of frontal attachment 32 that is disposed between rails 54, 56 to provide another sliding interface between frontal attachment 32 and body 30 that is transverse to venipuncture needle 50 and to fluid discharge needle 74. According to a satisfactory embodiment of the invention, venipuncture needle 50, a longitudinal bore through needle holder 68, an axial bore through fluid seal 72 and fluid discharge needle 74 are all coaxially alignable to establish a continuous fluid flow path through blood collection tube holder 22 during sampling of bodily fluids. The forwardly extending end of fluid discharge needle 74 is desirably seated just behind fluid seal 72 and is covered by flexible sheath 76 at any time that fluid discharge needle 74 is not inserted into and through the stopper of a fluid collection tube. Upon removal of a fluid collection tube from receptacle 40, flexible sheath 76 will again expand and desirably retain any blood or other bodily fluid either trapped or still flowing into tube holder 22 from a patient.

Referring to FIGS. 3 and 4, whenever a bodily fluid collection tube such as blood collection tube 24 (typically having one closed end 27 and one stoppered end 90) is inserted into the opening in the rear of receptacle 40 of body 30, fluid discharge needle 74 contacts and pierces stopper 90, which causes flexible sheath 76 to collapse to the position shown in FIG. 4. After locking needle cap 26 is removed and venipuncture needle 50 is inserted into a patient, blood can flow through needle 50, fluid seal 72 and fluid discharge needle 74 into evacuated reservoir 25 inside blood collection tube 74. Following collection of the sample in tube 24, it can be removed and another tube can be inserted to collect another sample or, if no further fluid samples are needed, body 30 can be shifted from the sample collection position to the needle retraction position without removing venipuncture needle 50 from the patient. For this reason, spring 66 of the needle retraction mechanism is desirably strong enough to retract needle holder 68 and needle 50 into needle retraction cavity prior to withdrawing venipuncture needle 50 from the vascular system of the patient. Although this method of use is preferred to reduce the likelihood of accidental needle sticks and the spread of blood-borne pathogens, venipuncture needle 50 can alternatively be removed from the patient prior to shifting either body 30 or frontal attachment 32 relative to the other along the sliding interface disposed between the two elements to initiate needle retraction.

Movement of body 30 and frontal attachment 32 relative to each other along the transverse sliding interface disposed between them is desirably achieved by applying oppositely directed manual or digital pressure to touchpad 44 of frontal attachment 32 and to the forward portion of the outwardly facing wall of needle retraction chamber 38 of body 30. Where venipuncture needle 50 is still inserted inside a patient, manual pressure is desirably applied to the outside wall of needle retraction chamber 38 while only applying resistance pressure to digital touchpad 44 of frontal attachment 32 so as not to cause venipuncture needle tip 52 to move while inserted in a patient's vein prior to needle retraction.

Referring again to FIGS. 1-9, as body 30 is moved laterally relative to frontal attachment 32 following use of tube holder 22, venipuncture needle 50 is carried by the needle retraction mechanism transversely from a first position where it was coaxially aligned with fluid seal 72 and fluid discharge needle 74 to a second position where it is coaxially aligned with the forwardly facing opening into bore 36 of needle retraction chamber 38. During the transverse movement, the rearwardly extending needle holder head 70 is biased by spring 66 into abutting contact with front surface 37 of body 30. As venipuncture needle 50 and needle holder 68 become coaxially aligned with bore 36 of needle retraction chamber 38, because the diameter of opening 34 is greater than the outside diameter of needle holder head 70 (FIG. 2), spring 66 expands further and drives needle holder 68 and venipuncture needle 50 upwardly into needle retraction chamber 38, thereby preventing needle tip 52 from any longer extending forwardly of nose 46 of frontal attachment 32 and rendering the device "safe" from accidental needle sticks. Similarly, because fluid discharge needle 74 is again covered by expanding flexible sheath 76 upon removal of blood collection tube 24 from receptacle 40, no pathogenically contaminated blood is subject to contact through the opening at the rearwardly facing end of receptacle 40.

Both body 30 and frontal attachment 32 are desirably molded from a moldable polymeric material suitable for the intended use. Fluid seal 72 is desirably made of an elastomeric polymer to facilitate expansion and contraction as needed to prevent leakage during use. If needed, an additional sealing element can be disposed around opening 35 to aid in preventing any fluid leakage during or after use. Venipuncture needle 50 is desirably secured inside needle holder 68 by any known conventional means such as, for example, by the use of glue or another adhesive that cures quickly under ultraviolet light or other radiation. Fluid discharge needle 74 is desirably held in place inside the fluid flow path through body 30 by glue or another adhesive composition, or by frictional engagement with either body 30 or fluid seal 72, or by the use of an additional seating element as discussed in greater detail below in relation to another embodiment of the invention.

Referring to FIGS. 10-16, a bodily fluid sampling device configured as blood collection tube holder 100 desirably comprises body 102 and frontal attachment 104 that are slidably engaged in such manner that body 102 can slide laterally relative to frontal attachment 104 along at least one sliding interface that is transverse relative to coaxially alignable venipuncture needle 124 and fluid discharge needle 150. Venipuncture needle 124 is held by needle holder 122 having longitudinal bore 123 and projects forwardly from nose 120 of frontal attachment 104 prior to and during use. Locking needle cap 130 (FIGS. 12-14) desirably covers venipuncture needle 124 prior to use, and is releasably secured to frontal attachment 104 by frictional engagement between the inside of attachment collar 136 and the plurality of circumferentially spaced-apart, longitudinally extending ribs 126 disposed around nose 120. In this embodiment, locking arm 132 of locking needle cap 130 is configured and positioned so that it is releasably engageable with a recess defined by an additional forwardly facing, small-diameter opening 134 disposed between oval-shaped opening 114 into needle retraction chamber 108 and larger-diameter opening 156 that is located in front wall 154 of cylindrical receptacle 106 of body 102.

Figure 12:
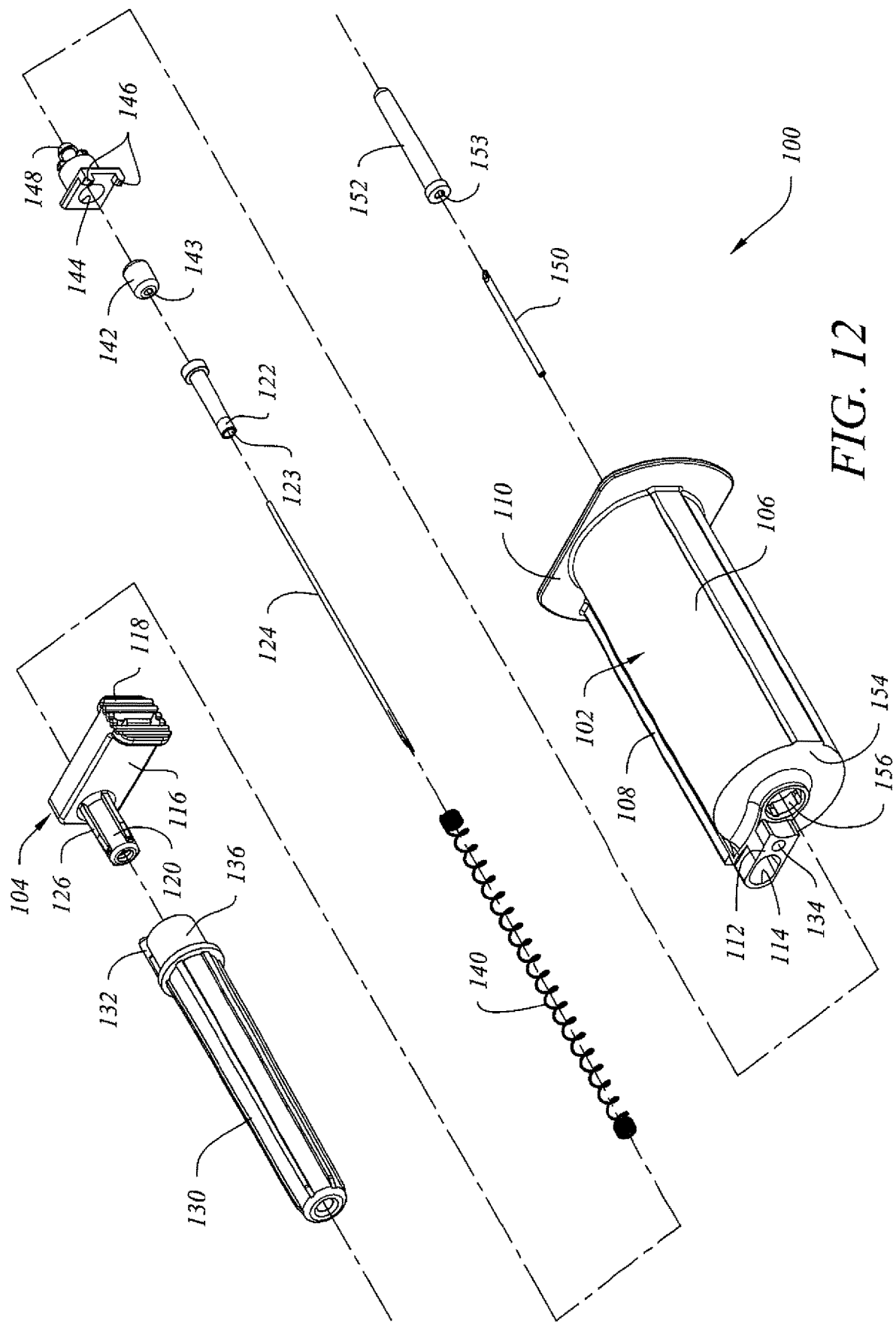
FIG. 12 is an exploded top front perspective view of the medical device of FIG. 10, also showing a locking needle cap that is not depicted in FIG. 10.
Figure 14:
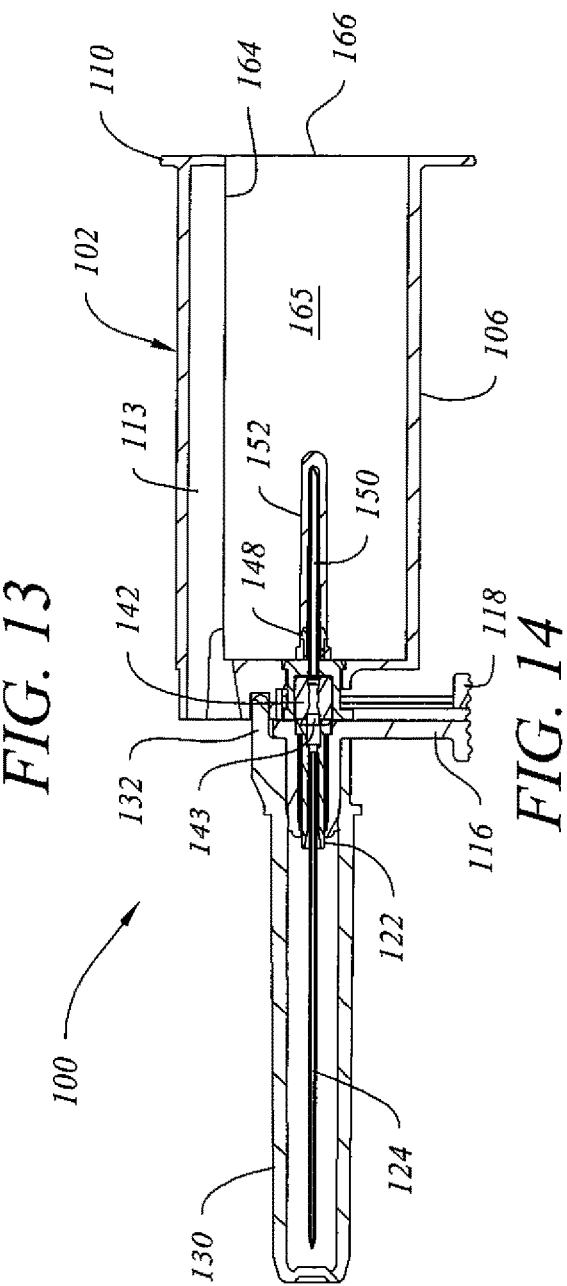
FIG. 14 is a cross-sectional view taken along line 14-14 of FIG. 10, but rotated 90°.

In this embodiment of the invention, a needle retraction mechanism comprising needle holder 122 and compression spring 140 are desirably against seated inside frontal attachment 104 as previously described in relation to the embodiment of FIGS. 1-9, and elastomeric fluid seal 142 containing coaxial fluid passage 143 is against disposed between body 102 and frontal attachment 104. Referring to FIGS. 12, 14, fluid seal 142 is seated in opening 144 inside attachment element 148 that supports and seats fluid discharge needle 150 and base 153 of flexible sheath 152. During assembly of blood collection tube holder 100, attachment element 148 (with fluid discharge needle 150 and flexible sheath 152 already attached) is satisfactorily inserted and seated inside larger-diameter opening 156 by frictional engagement or by the use of a suitable adhesive if desired. Frontal attachment 104 is then attachable to attachment element 148 seated inside body 102 in such manner that upper and lower engagement arms 146 slidably engage at least one laterally extending support rail disposed on the rearwardly facing side of body 116 of frontal attachment 104. Similarly, the back side of body 16 desirably comprises laterally extending sliding surfaces that slidably engage top, bottom or forwardly facing surfaces 112 of body 102 to facilitate transverse slidable engagement of frontal attachment 104 with body 102 along at least one sliding interface disposed between frontal attachment 104 and body 102.

Figure 13:
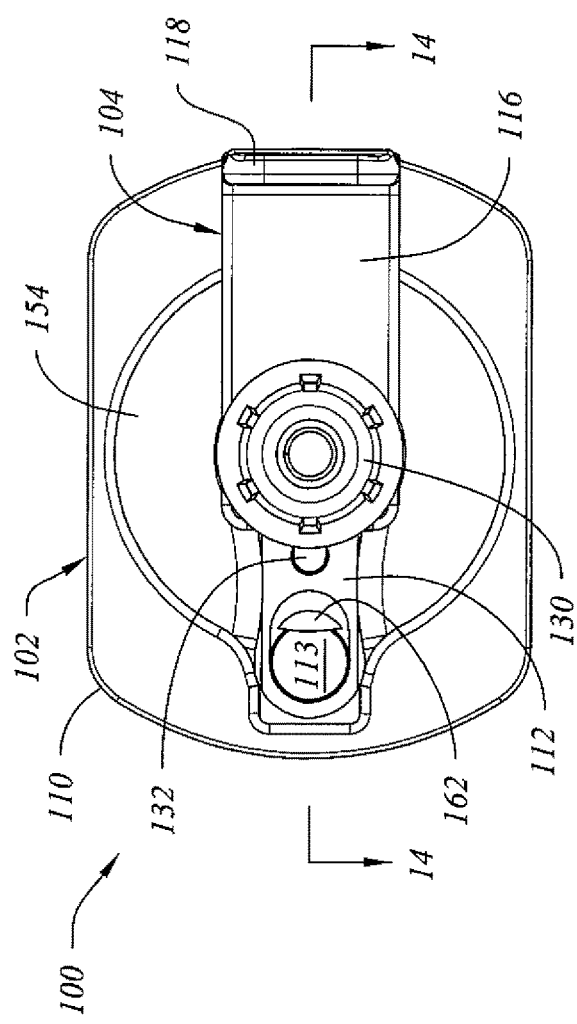
FIG. 13 is a front elevation view of the medical device of FIG. 10 with the locking needle cap of FIG. 12 attached.

Referring to FIGS. 12-14, forwardly facing oval-shaped opening 114 comprises an inclined ramp section 162 communicating between opening 114 and the remainder of needle retraction cavity 113 inside needle retraction chamber 108. Inclined ramp section 162 serves as guide to begin directing needle holder 122 and spring 140 into needle retraction cavity 113 as body 102 is moved laterally across the face of frontal attachment 104 to a point where needle holder 122 and venipuncture needle 124 are no longer coaxially aligned with fluid seal 142 and fluid discharge needle 150 during the needle retraction process after the desired fluid sample(s) are drawn. It is be noted, however, that FIG. 13 depicts blood collection tube holder 100 before any sample is drawn because locking needle cap 130 is still in place, ramp section 162 is fully visible, and body 102 is not shifted laterally relative to frontal attachment 104 as previously described in relation to the embodiment of FIGS. 1-9.

Figure 15:
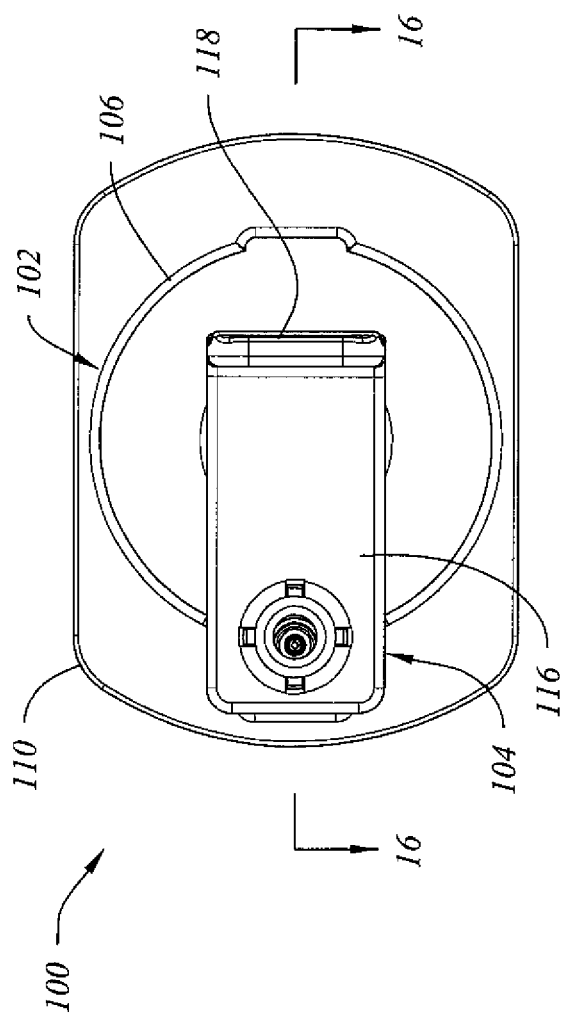
FIG. 15 is a front elevation view of the medical device of FIG. 10 following transverse repositioning of the body relative to the frontal attachment and retraction of the needle.
Figure 16:
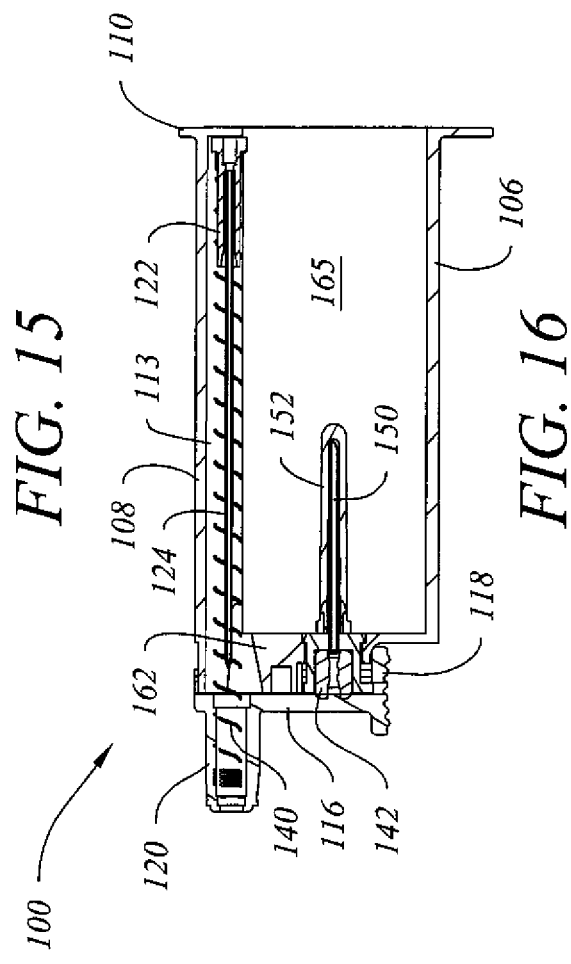
FIG. 16 is a cross-sectional view taken along line 16-16 of FIG. 15, but rotated 90°.

Referring to FIGS. 15-16, body 102 is repositioned relative to frontal attachment 104 by the application of oppositely directed manual pressure against touchpad 118 and the outside wall of needle retraction chamber 113. When repositioned in this manner, which can precede or follow removal of a bodily fluid collection tube (used in sampling bodily fluids such as blood) from interior 165 of cylindrical receptacle 106 through a rearwardly facing opening in flange 110, venipuncture needle 124 is no longer coaxially alignable with fluid discharge needle 150, and the fluid pathway from venipuncture needle 124 through fluid seal 142 and fluid discharge needle 150 is blocked by body 116 of frontal attachment 104. As seen in FIG. 16, spring 140 then expands to force needle holder 122 and at least a major portion of venipuncture needle 124 into needle retraction cavity 113 inside needle retraction chamber 108 so that no portion of needle 124 projects forwardly from nose 120, rendering the device "safe" against accidental needle sticks and the associated risks of pathogenic contamination and the spread of disease.

Referring to FIGS. 17-21, a bodily fluid sampling device configured as blood collection tube holder 200 desirably comprises body 202 and frontal attachment 204 that are slidably engageable in such manner that body 202 can slide laterally relative to frontal attachment 204 along at least one sliding interface that is transverse relative to coaxially alignable venipuncture needle 232 and fluid discharge needle 225. In this embodiment of the invention, cylindrical receptacle 216 configured to receive a bodily fluid collection tube (not shown) is made separately from body 202 and is selectively attachable to body 202 by a threaded connector 226 that is integrally molded as part of body 202. Although a threaded connection is shown, it should be understood that other similarly effective connector configuration can also be used within the scope of the invention. Thus, for example and without limitation, a snap connector or bayonet-type connector can also be provided, although the connector portions of body 202 and cylindrical tube receptacle 216 are desirably cooperatively sized and configured. Tip 228 disposed rearwardly of threaded connector 226 is configured to receive and frictionally engage and seat flexible sheath 227 when sheath 227 is placed over fluid discharge needle 225.

Figure 17:
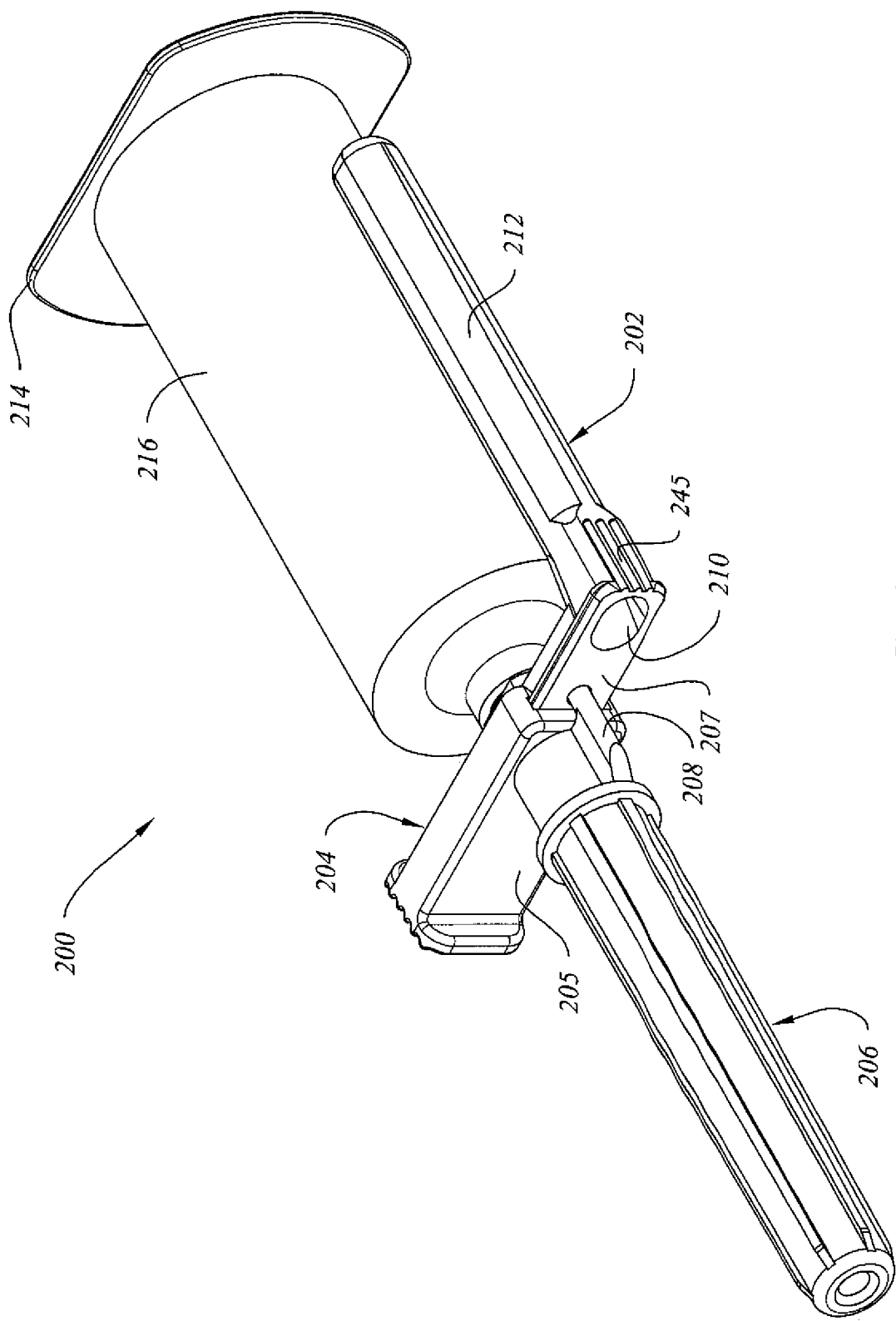
FIG. 17 is a top front perspective view of another embodiment of a medical device of the invention (with a locking needle cap installed over the forwardly projecting needle) that is shown with the body connected to a separate fluid collection tube holder.
Figure 18:
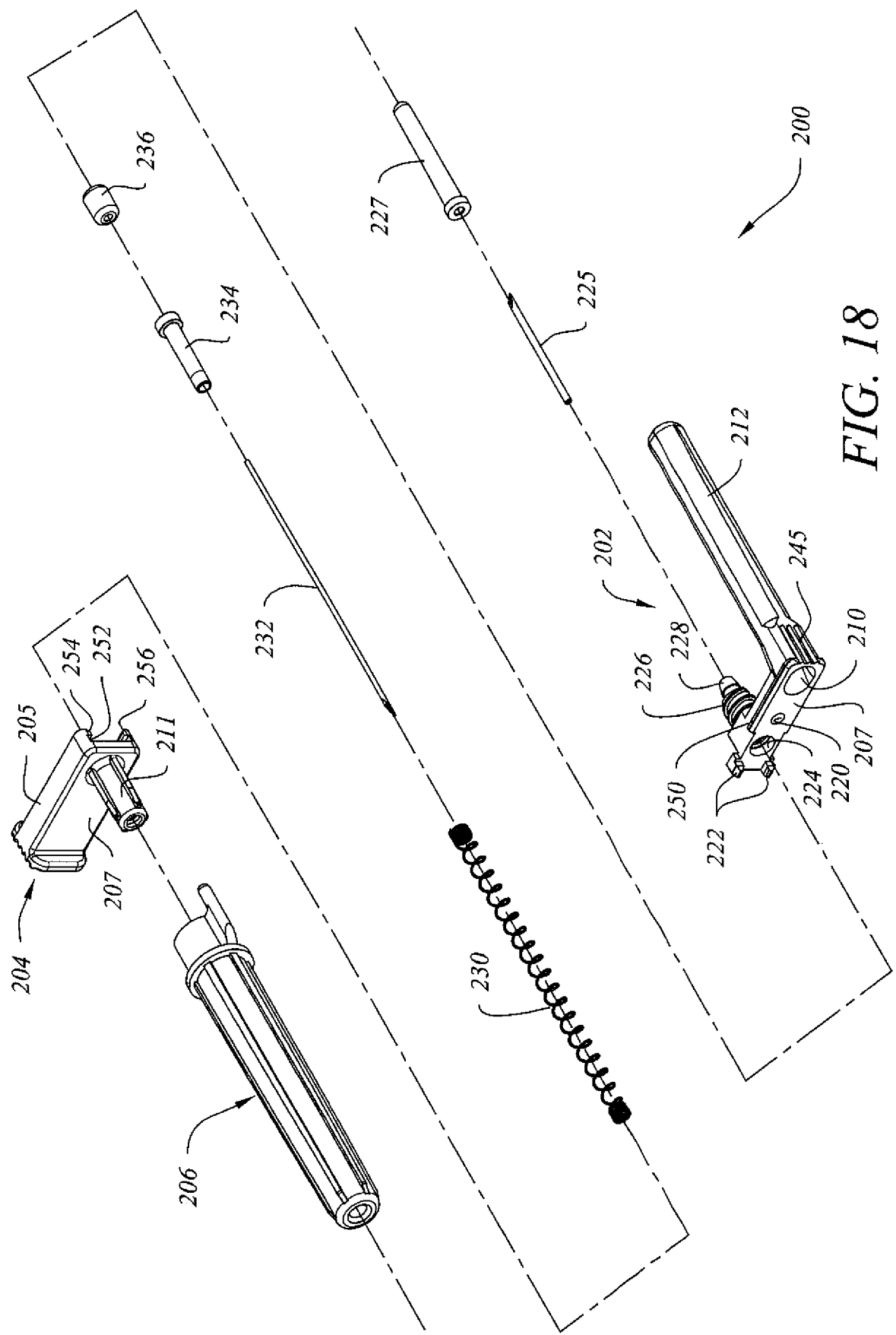
FIG. 18 is an exploded top front perspective view of the medical device of FIG. 17 but not showing the fluid collection tube holder.
Figure 19:
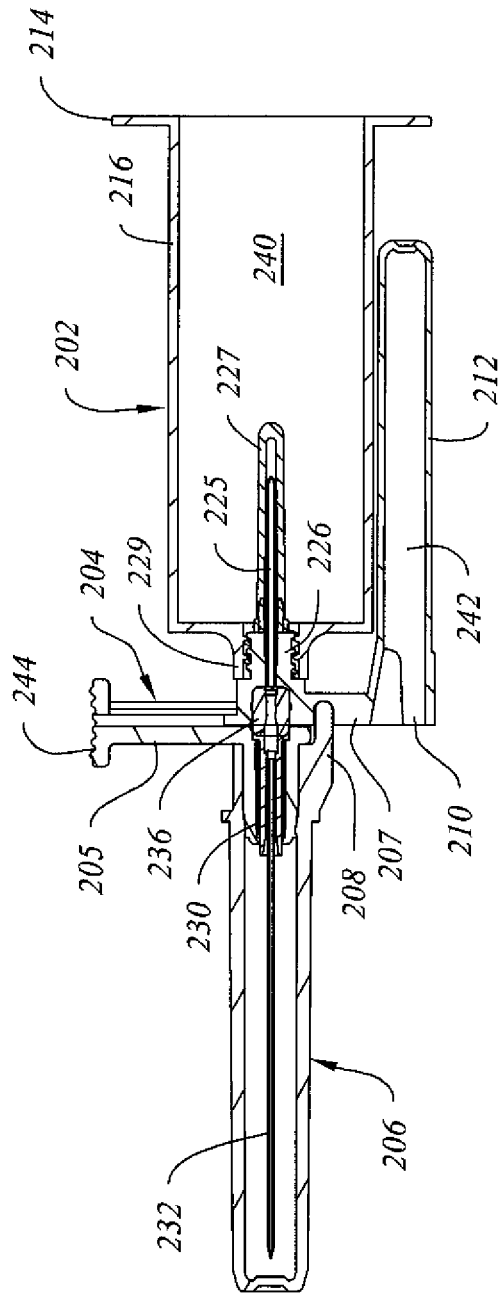
FIG. 19 is a cross-sectional plan view of the medical device of FIG. 17, again showing the body connected to a fluid collection tube holder.

Referring to FIGS. 17-19, blood collection tube holder 200 comprises body 202, slidably engageable frontal attachment 204 and locking needle cap 206 with locking arm 208. Frontal attachment 202 further comprises top and forwardly facing surfaces 205, 207, top and bottom rearwardly facing rails 254, 256 defining a recess 252 adapted to slidably engage cooperatively sized and configured rails 250 on the top and bottom of body 202 to facilitate lateral sliding movement of body 202 relative to frontal attachment 204 along a sliding interface that is transverse to the longitudinal axis through forwardly facing venipuncture needle 232 and coaxially alignable, rearwardly facing fluid discharge needle 225. A needle retraction assembly comprising compression spring 230 and needle holder 234 are configured and installed in frontal attachment 204 as previously described. Cylindrical fluid seal 236 comprises a fluid pathway suitable for establishing fluid communication between venipuncture needle 232 and needle holder 234 on the front side and with fluid delivery needle 225 on the back side. Flexible sheath 227, which is pierceable by fluid discharge needle 225, is provided to cover fluid delivery needle 225 when it is not inserted into a fluid collection tube. Forwardly facing openings 210, 220 and 224 in forwardly facing surface 207 of body 202 provide front access to needle retraction chamber 212, to a recess behind opening 220 for locking arm 208, and to fluid discharge needle 232, respectively.

Body 202 further comprises needle retraction chamber 212 having a digital touchpad 245 that is visible on the side facing away from top and bottom engagement arms 222 that cooperate with top and bottom rails 250 to facilitate lateral sliding engagement between body 202 and frontal attachment 204. Repositioning of body 202 relative to frontal attachment 204 is achieved when venipuncture needle 232 is still inserted in a patient by applying digital pressure to touchpad 245 while manually applying oppositely directed resistance to touchpad 244. Alternatively, if venipuncture needle 232 is withdrawn from the patient prior to initiating needle retractions, frontal attachment 204 can be repositioned relative to body 202 by simultaneously applying oppositely directed pressure to both of touchpads 244, 245 to "squeeze" body 202 and frontal attachment in opposite directions along the sliding interface between them until needle holder 234 is aligned with opening 210 to complete retraction of needle 232.

Figure 20:
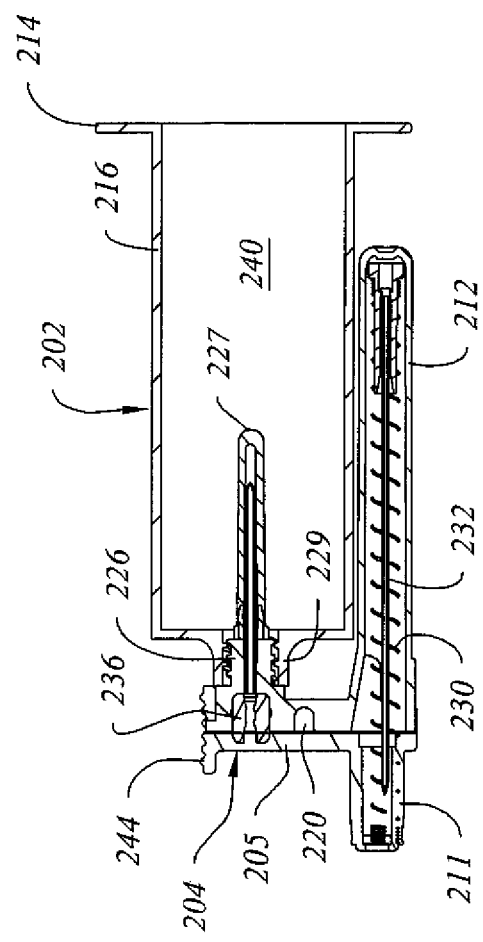
FIG. 20 is the medical device of FIG. 19 following removal of the locking needle cap, transverse repositioning of the body relative to the frontal attachment and retraction of the forwardly projecting needle.
Figure 21:
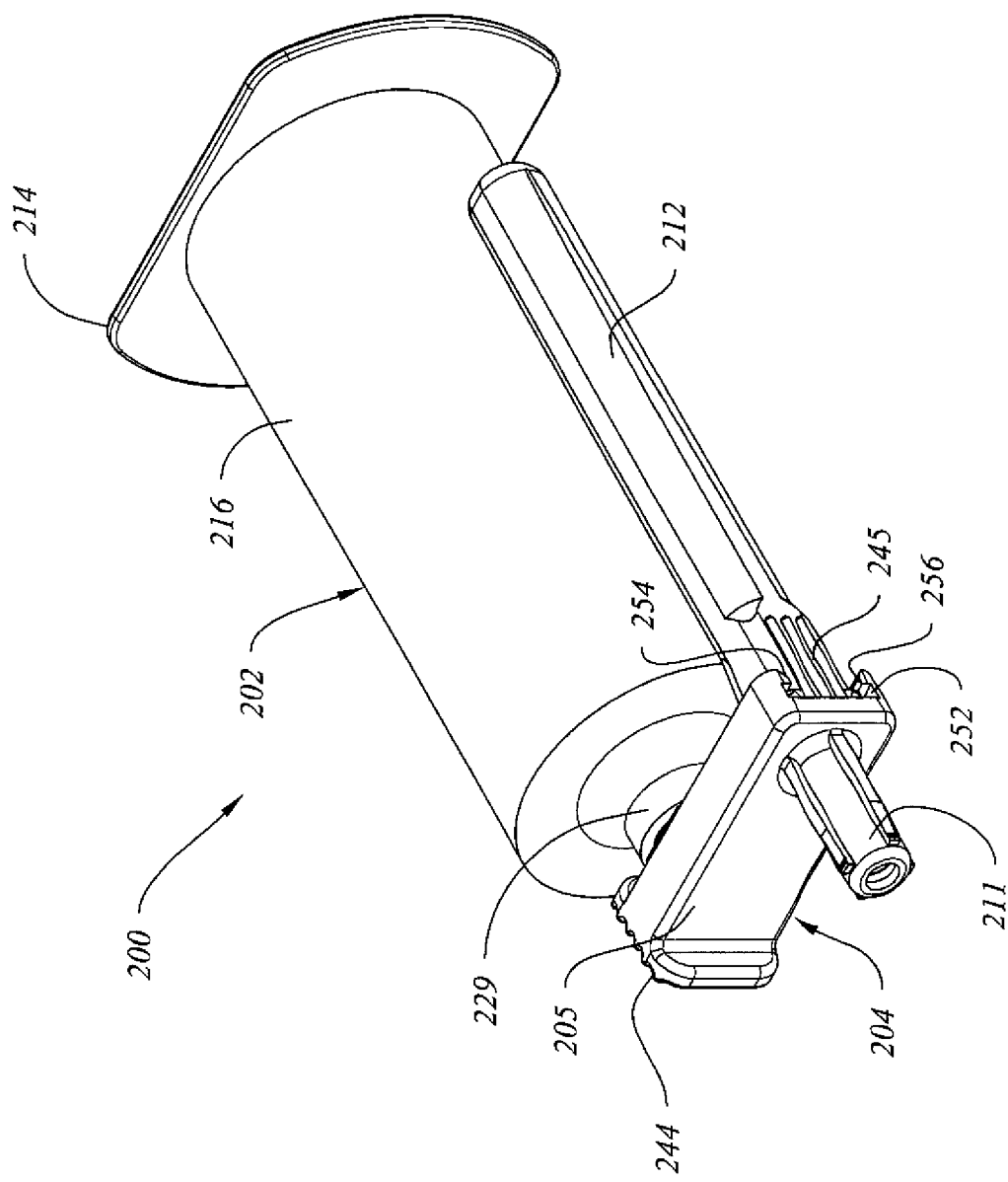
FIG. 21 is a top front perspective view of the medical device of FIG. 17.

Referring to FIGS. 20-21, cylindrical receptacle 216 comprising an opening defined by rear flange 214 and containing interior volume 240 has a forwardly facing neck 229 comprising female threads configured to engage cooperatively threaded male connector 226 projecting rearwardly from body 202 in laterally spaced-apart relation to needle retraction chamber 212 containing needle retraction cavity 242. Sufficient lateral clearance is desirably provided between threaded connector 226 and needle retraction chamber 212 to permit a cylindrical receptacle 216 of suitable diameter to be positioned between them.

Figure 22:
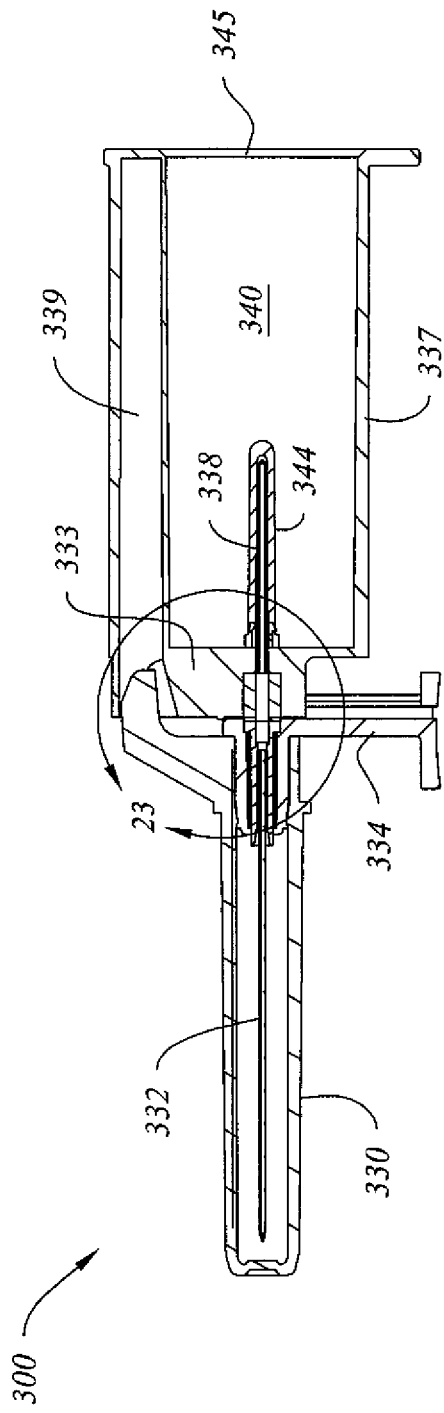
FIG. 22 is a plan view of another embodiment of a medical device of the invention wherein a friction element is provided to reduce the likelihood of accidental transverse repositioning of the body relative to the frontal attachment.
Figure 23:
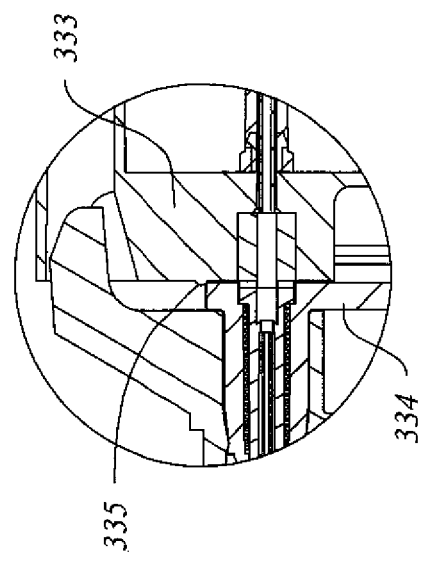
FIG. 23 is an enlarged detail view taken from FIG. 22.

Referring to FIGS. 22 and 23, another embodiment of the invention is disclosed as blood collection tube holder 300 comprising body 333 with cylindrical receptacle 337 having interior volume 340 accessed through open end 345, needle retraction cavity 339, and a rearwardly projecting fluid discharge needle 338 surrounded by flexible sheath 344. Slidably engaging the forwardly facing end of body 333 is frontal attachment 334 comprising forwardly projecting venipuncture needle 332 that is protected in the position shown by locking needle cap 330. Referring to the detail view shown as FIG. 23, an interference element 335 in the configuration of a small projection extending forwardly from body 333 is provided to reduce the likelihood that relative lateral movement will accidentally occur between body 333 and frontal attachment 334 after locking needle cap 330 and its associated locking arm are removed from blood collection tube holder 300 but prior to or during use.

Although interference element 335 is depicted as a small projection that can be molded as part of body 333, it will be appreciated upon reading this disclosure that other similarly effective structures such as for example, another rupturable, breakable, frangible, frictional or displaceable physical barrier, can also be used in the invention to reduce the likelihood of accidental or inadvertent, premature lateral movement of the body 333 or frontal attachment 334 relative to the other.

Figure 24:
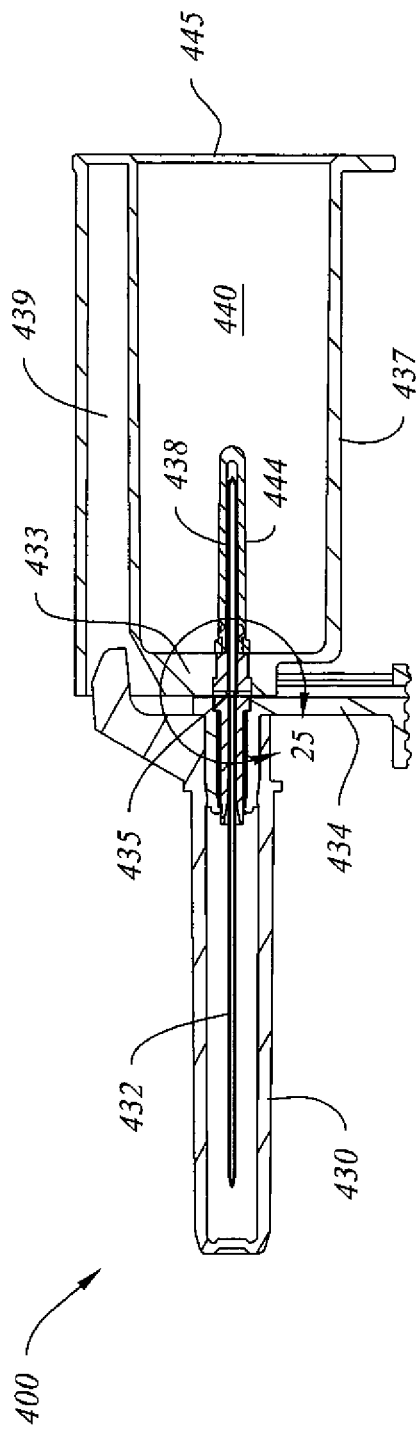
FIG. 24 is a plan view of another embodiment of a medical device of the invention wherein a breakable or severable link is provided between the body and the frontal attachment to reduce the likelihood of accidental transverse repositioning of the body relative to the frontal attachment.
Figure 25:
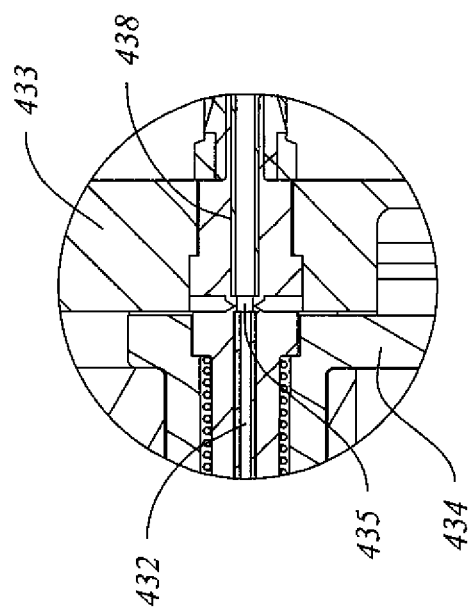
FIG. 25 is an enlarged detail view taken from FIG. 24.

Referring to FIGS. 24 and 25, another embodiment of the invention is disclosed as blood collection tube holder 400 comprising body 433 with cylindrical receptacle 437 having interior volume 440 accessed through open end 445, needle retraction cavity 439, and a rearwardly projecting fluid discharge needle 438 surrounded by flexible sheath 444. Slidably engaging the forwardly facing end of body 433 is frontal attachment 434 comprising forwardly projecting venipuncture needle 432 that is protected in the position shown by locking needle cap 430. Referring to the detail view shown as FIG. 25, in this embodiment of the invention, a small flash chamber 435 is disclosed between the rearwardly facing end of venipuncture needle 432 and the forwardly facing end of fluid discharge needle 438.

Other alterations and modifications of the apparatus disclosed here will become apparent to those of ordinary skill in the art upon reading this specification in relation to the accompanying drawings, and the inventors intend that the scope of the invention be limited only by the broadest interpretation of the appended claims to which the inventors are legally entitled.

We claim:

1. A blood collection tube holder comprising:
   a body further comprising a rearwardly facing fluid discharge needle and a needle retraction chamber laterally spaced apart from the fluid discharge needle; and
   a frontal attachment disposed in transverse sliding relation to the body, the frontal attachment comprising a needle retraction mechanism further comprising a forwardly projecting venipuncture needle that is coaxially aligned with the rearwardly facing fluid discharge needle when the body is disposed in a first position relative to the frontal attachment and that is coaxially aligned with and retractable into the needle retraction chamber when the body is repositioned laterally to a second position relative to the frontal attachment.

2. The blood collection tube holder of claim 1 further comprising a cylindrical receptacle projecting rearwardly from the body, the cylindrical receptacle being configured to receive and support a blood collection tube.

3. The blood collection tube holder of claim 1 further comprising a flash chamber disposed between the venipuncture needle and the fluid discharge needle.

4. The blood collection tube holder of claim 1 wherein the needle retraction mechanism is a needle retraction assembly seated inside the frontal attachment.

5. The blood collection tube holder of claim 4 wherein the needle retraction assembly comprises a needle holder that is rearwardly biased in relation to the frontal attachment.

6. The blood collection tube holder of claim 5 wherein the venipuncture needle is disposed in fluid communication with the needle holder.

7. The blood collection tube holder of claim 1 wherein the fluid discharge needle is seated in fixed relation to the body.

8. The blood collection tube holder of claim 1 wherein the venipuncture needle is selectively retractable relative to the frontal attachment.

9. The blood collection tube holder of claim 2 wherein the fluid discharge needle is configured to be insertable into fluid communication with the blood collection tube.

10. The blood collection tube holder of claim 2 wherein the generally cylindrical receptacle is attachable to the body.

11. The blood collection tube holder of claim 10 wherein the generally cylindrical receptacle threadedly engages the body.

12. The blood collection tube holder of claim 1 wherein the needle retraction chamber has a forwardly facing opening.

13. The blood collection tube holder of claim 2 wherein the needle retraction chamber shares a common wall with the generally cylindrical receptacle and is molded as part of the body.

14. The blood collection tube holder of claim 1 wherein the frontal attachment slidably engages the body along a transverse interface that is substantially perpendicular to the rearwardly facing fluid discharge needle and extends at least from the fluid discharge needle to the needle retraction chamber.

15. The blood collection tube holder of claim 14 wherein relative sliding movement between the frontal attachment and the body can be initiated by applying oppositely directed digital pressure to the frontal attachment and the body, respectively.

16. The blood collection tube holder of claim 15 wherein the oppositely directed digital pressure is applied to oppositely facing touchpads disposed on the frontal attachment and the body, respectively.

17. The blood collection tube holder of claim 1 further comprising at least one interference element disposed between the frontal attachment and the body to mechanically impede relative sliding movement between the frontal attachment and the body prior to retracting at least part of the first needle into the needle retraction chamber.

18. The blood collection tube holder of claim 17 wherein sliding movement is initiated by manually over-pressuring the interference element.

* * * * *